US006451332B1

United States Patent
Tanaka et al.

(10) Patent No.: US 6,451,332 B1
(45) Date of Patent: *Sep. 17, 2002

(54) PESTICIDAL COMPOSITION HAVING HIGH PESTICIDAL INGREDIENT VAPORIZATION RATE METHOD FOR CONTROLLING PESTS, AND METHOD FOR PRODUCING A PESTICIDAL COMPOSITION

(75) Inventors: Yasuyori Tanaka, Toyonaka; Yasuyuki Katayama, Chiba, both of (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 47 days.

(21) Appl. No.: 09/208,413

(22) Filed: Dec. 10, 1998

(30) Foreign Application Priority Data

Dec. 16, 1997 (JP) .............................................. 9-346202

(51) Int. Cl.⁷ .......................... A01N 25/00; A61K 9/72; A61K 31/18
(52) U.S. Cl. .......................... 424/405; 424/40; 514/601
(58) Field of Search .................... 424/405, 40; 514/601

(56) References Cited

U.S. PATENT DOCUMENTS

| 3,948,987 A | * | 4/1976 | Fridinger ................. 260/397.6 |
| 4,228,124 A | * | 10/1980 | Kashihara et al. ............. 422/36 |
| 5,364,966 A | * | 11/1994 | Kisida et al. ................. 564/190 |
| 5,807,539 A | * | 9/1998 | Tsukii et al. .................. 424/40 |

FOREIGN PATENT DOCUMENTS

| JP | 53-109945 | | 9/1978 |
| JP | 63267705 | * | 11/1988 |

OTHER PUBLICATIONS

CA plus Abstract AN: 1983:67132, Sumitomo Chemical, 1983.*
Grasshoff et al., *World Patents Index*, vol. 72, #64802, 1972.*
Tsukii et al., *Chemical Abstracts*, vol. 122, #181029, 1996.*
Shelhime et al., *Chemical Abstracts*, vol. 75, #34463, 1976.*

* cited by examiner

Primary Examiner—Russell Travers
Assistant Examiner—Shengjun Wang
(74) Attorney, Agent, or Firm—Sughrue Mion, PLLC

(57) ABSTRACT

A pesticidal composition comprising the pesticidal ingredient, which is solid at room temperature and has a grain size of 30 μm or less in volume median diameter, and an organic foaming agent has a high vaporization rate and show a high pest-controlling effect.

1 Claim, 1 Drawing Sheet

PESTICIDAL COMPOSITION HAVING HIGH PESTICIDAL INGREDIENT VAPORIZATION RATE METHOD FOR CONTROLLING PESTS, AND METHOD FOR PRODUCING A PESTICIDAL COMPOSITION

This application claims foreign priority of JP application 09-346202, filed Dec. 16, 1997.

BACKGROUND OF THE INVENTION

The present invention relates to a pesticidal composition. Japanese Laid-open patent No. sho-53-109945A and Japanese Examined patent No. sho-61-33001B disclose a method wherein a pesticidal composition fumigates to control pests. However, the methods disclosed in the said patents do not efficaciously control pests when a solid pesticidal ingredient is employed in the pesticidal composition.

Based on prior pest controlling methods, a pesticidal composition comprising of a solid pesticidal ingredient that has a low vaporization rate, is not available. A lower vaporization rate distributes a smaller dosage of the pesticidal ingredient and consequently procures an ineffective pest controlling performance.

SUMMARY OF THE INVENTION

The present invention relates to a pesticidal composition particularly against mites and cockroaches inhabiting an indoor environment. When the pesticidal composition is fumigated, a high amount of the pesticidal ingredient is released to control pests such as cockroaches and mites effectively. The present invention employs the pesticidal ingredient as a multiplicity of solid granules wherein the volume median diameter is 30 μm or less.

DETAILED DESCRIPTION OF THE INVENTION

The pesticidal ingredient utilized for the present invention is a solid at room temperature. The grain of the pesticidal ingredient powder has a volume median diameter of 30 μm or lower, and generally the powder, the grain size of which is 3 to 30 μm in volume median diameter, may be utilized. The employment of the pesticidal ingredients is generally not restricted, but a condition wherein 70% or more of the grain of the pesticidal ingredient powder have a diameter of 30 μm or less is preferable. As used herein, the volume median diameter is the diameter wherein an equal total volume of grains with greater and lesser c grain diameters are present, when the grains are arranged in order of magnitude of grain diameter. The volume median diameter can be measured by laser diffraction method.

The present invention may employ sulfonanilide insecticidal/acaricidal compounds such as 2-methoxy carbonyl-4-chlorotrifluoromethanesulfonanilide, pyrethroidal compounds such as (S)-2-methyl-4oxo-3-(2-propynyl) cyclopent-2-enyl (1R)-trans-3-(2,2-dichlorovinyl)-2,2-dimethylcyclopropanecarboxylate, tetramethrin, carbamate compounds such as metoxadiazone, neonicotinoids such as acetamiprid [(E)-N1-((6-chloro-3-pyridinyl)methyl)-N2-cyano-N1-methylacetamidine], nitenpyram [N-((6-chloro-3-pyridinyl)methyl)-N-ethyl-N'-methyl-2-nitro-1,1-ethylenediamine], thiaclopid [(3-((6-chloro-3-pyridinyl) methyl)-2-thiazolidinylidene)cyanamide], thiamethoxam [3-((2-chloro-5-thiazolyl)methyl)-5-methyl-4-nitroiminotetrahydro-1,3,5oxadiazine], chlothianidine [1-(2-chloro-5-thiazolyl)methyl-3-methyl-2-nitroguanidine] and 1-(tetrahydrofuran-3-yl)methyl-3-methyl-2-nitroguanidine, etoxazole [5-tert-butyl-2-[2-(2,6-difluorophenyl)-4,5-dihydro-1,3-oxazol-4-yl]phenetole], and/or so on as the pesticidal ingredient. The amount of the pesticidal ingredients is generally 1% to 25% by weight based on the total amount of the present composition.

The present invention may employ various organic foaming agents, but an organic foaming agent wherein the heat decomposition thereof generates gas usually is employed. More specifically, an,organic foaming agent wherein the gas generated from thermal decomposition is nitrogen and wherein the foaming temperature is 300° C. or less is usually employed. Azodicarbonamide; p-toluenesulfonylhydrazide; benzenesufonylhydrazide; p,p'-oxybis (benzenesulfonylhydrazide); azobisisobutyronitrile; 2,2'-azobisisobutyroamide; 2-(carbamoylazo)isobutyronitrile; methyl-2,2'-azobisisobutyrate; 2,4-bis(azosulfonyltoluene); 1,1'-azobiscyclohexanecarbonitrile; dinitrosopentamethylenetetramine, and so on are examples of possible organic foaming agents that may be employed for the present invention. The organic foaming agents thereof are generally employed as powdery material of about 50 to 200 mesh. The amount of the organic foaming agents is generally 10% to 97% by weight based on the total amount of the present composition.

The pesticidal ingredient and the organic foaming agent may be mixed in various methods to obtain the pesticidal composition, but it is preferable to mix the pesticidal ingredient and the organic foaming agent homogeneously to achieve a higher vaporization rate of the pesticidal ingredient. More specifically, after an appropriate amount of water is added to a mixture of the pesticidal ingredient and organic foaming agent, the mixture may be formed to granules wherein the granular diameter is 1 to 4 mm, preferably a granular diameter of 1.5 mm to 3 mm, and dried. The mixture preferably contains a temperature controlling agent and/or a binder described below.

Grinders/pulverizers such as a centrifugal grinder/pulverizer, jet mill, hammer mill, pin mill, ball mill and oscillating grinders/pulverizers may be utilized to break down the pesticidal ingredients into finer powder, so that the volume median diameter is 30 μm or less.

The pesticidal composition may also comprise of fragrance materials; deodorants; synergists such as piperonyl butoxide, N-(2-ethylhexyl)bicyclo[2.2.1]hept- 5-ene-2,3-dicarboximide, N-(2-ethylhexyl)-1-isopropyl-4-methylbicyclo[2.2.2]oct-5-ene-2,3-dicarboximide, octachlorodipropylether; and so on, in addition to the organic foaming agent and the pesticidal ingredient.

Furthermore, the temperature wherein the organic foaming agent is decomposed, may be controlled by incorporating temperature controlling agents such as zinc oxide, zinc carbide, urea, chrome yellow, carbon black, zinc stearate, and/or calcium stearate. Even further, uniform consistency or solidification may be improved by the incorporation of binder(s). Starch, natural polymers, synthetic polymers, and so on are examples of binders. Examples for the said natural polymers are tragacanth gum, gum arabic, guar gum, powdered gambier extraction, casein, and a mixture thereof. Examples for the said synthetic polymers are polyvinyl alcohol, polyacrylamide, sodium polyacrylate, polyethylene oxides, polyvinylpyrrolidone, methylcellulose, ethylcellulose, hydroxyethylcellulose, hydroxypropylcellulose, carboxymethylcellulose salts, carboxymethylstarch salts, dialdehydestarch, cationic starches and a mixture thereof. The amount of the temperature controlling agent and binder is generally 0.1 to 10% and 0.1 to 5% by weight based on the total amount of the present composition respectively.

It is preferable that thermal decomposition of the organic foaming agent is accomplished by the heat of a chemical reaction. For example, the pesticidal composition may be placed in a container that is made of good heat conductivity, like metal, so the pesticidal composition may be heated through the said container. Once the pesticidal composition is heated to the appropriate temperature, the organic foaming agent is decomposed and generates gas and the pesticidal ingredient is blown down and vaporized into the environment.

More specifically, a device set forth in FIG. 1 may be utilized to heat the pesticidal composition. The pesticidal composition 1 is placed interior to the separating wall 4 wherein calcium oxide 3 is placed in a position that is exterior to the separating wall. An appropriate amount of water may then be poured to the calcium oxide through a water entrance 5 to cause the calcium oxide-water reaction that heats the pesticidal composition. Once the pesticidal composition reaches the appropriate temperature, the organic foaming agent will decompose and generate gas, and the pesticidal ingredient will be blown down and vaporized.

Figure 1:
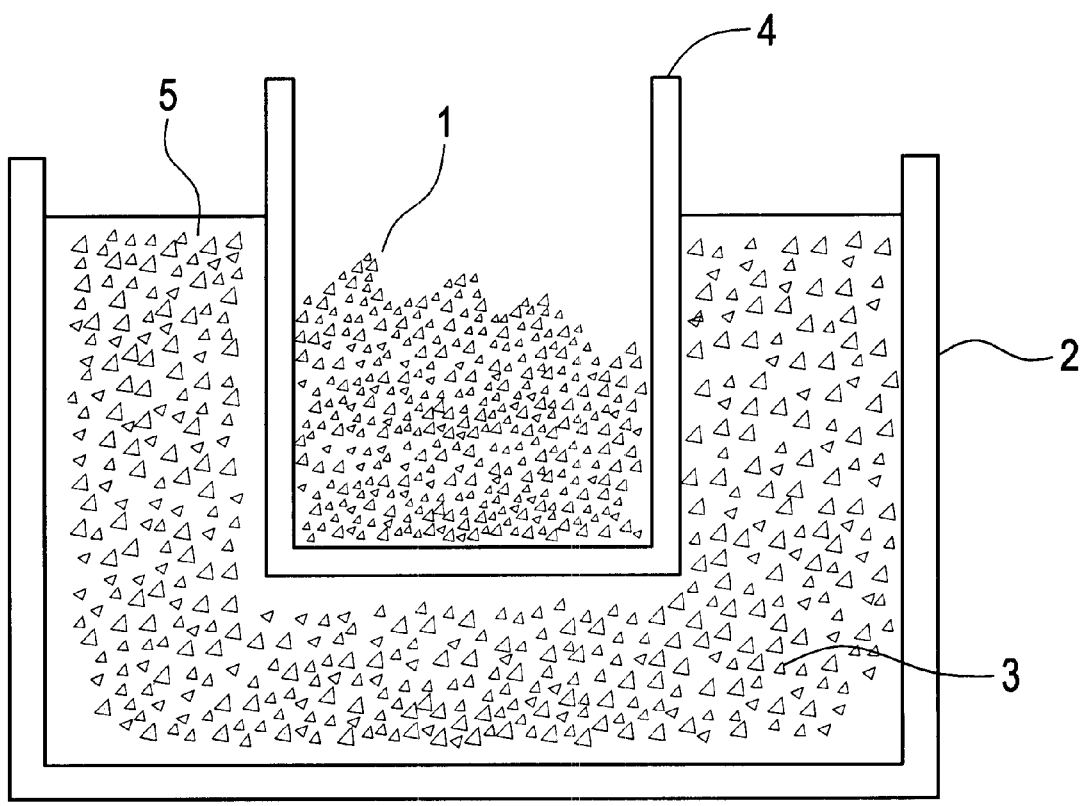
FIG. 1 is a presentation by a cross section of one example of a device wherein the pesticidal composition of the present invention is utilized to perform a pest controlling.

Numeral 2 designates the container to hold the pesticidal composition. In the container, the pesticidal composition 1 of the present invention and calcium oxide 3 are set separated by the wall 4. Numeral 5 designates water entrance.

EXAMPLES

Production of the Pesticidal Composition

Example 1

2-methoxycarbonyl-4-chlorotrifluoromethanesulfonanilide was broken down in a centrifugal grinder/pulverizer to obtain powder. The acquired powder was then measured on the SALD 1100 (Shimadzu Corporation; a direct calculating method that utilizes method of least squares based from the laser diffraction method). The volume median diameter was 11.6 $\mu$m and the percentage of grain with a diameter of 30 $\mu$m or less was 96.0% 7.7 parts by weight of the powder of 2-methoxycarbonyl-4-chlorotrifluoromethanesulfonanilide, 0.5 parts by weight of zinc oxide, 2.0 parts by weight of α-starch, and an appropriate amount of azodicarbonamide were incorporated to make the total 100 parts by weight. After adding water to the resulting mixture, the said mixture was kneaded, formed to granular material with an extruder, and dried to obtain the pesticidal composition of the present invention.

Example 2

Tetramethrin was broken down in a centrifugal grinder/pulverizer to obtain powder. The acquired powder was then measured on the SALD 1100 (Shimadzu Corporation; a direct calculating method that utilizes method of least squares based from the laser diffraction method). The volume median diameter was 28.5 $\mu$m. 7.7 parts by weight of the obtained tetramethrin, 0.5 parts by weight of zinc oxide, 2.0 parts by weight of α-starch, and an appropriate amount of azodicarbonamide were incorporated to make the total 100 parts by weight. After adding water to the resulting mixture, the said mixture was kneaded, formed to granular material with an extruder, and dried to obtain the pesticidal composition of the present invention.

Reference Example 3

2-methoxycarbonyl-4-chlorotrifluoromethanesulfonanilide was broken down and measured in the same way as example 1. The acquired powder had grains of a volume median diameter of 35 $\mu$m. The pesticidal composition for reference was then obtained in the way recited in example 1.

Reference Example 4

Two parts by weight of α-starch, 0.5 parts by weight of zinc oxide, and an appropriate amount of azodicarbonamide were incorporated to make the total 92.3 parts by weight. After incorporating water to the resulting mixture, the said mixture was then kneaded, formed to granular material with an extruder, and dried. A solution wherein 7.7 parts by weight of 2-methoxycarbonyl-4-chlorotrifluoromethanesulfonanilide was diluted in a small amount of acetone, was soaked onto the dried granular and then evaporated acetone to obtain the pesticidal composition for reference.

Test Example 5

A pesticidal device was prepared by having:
1) 10 g of the pesticidal composition obtained in example 1 placed interior to the separating wall of the container presented in FIG. 1 and
2) 100 g of calcium oxide with 1–20 mesh placed exterior to the said separating wall but within the said container.

Three polyethylene cups were then prepared by freeing 5 male and 5 female German cockroaches (*Blattella germanica*) into each cup. Each said cup was then placed at a designated location in a large chamber (28 m$^3$). The pesticidal device was then located in the central region of the large chamber. Subsequently, water was poured to the said calcium oxide so the device would be heated. All the German cockroaches were dead after one day.

Test Example 6

Ten grams (10 g) of the pesticidal composition obtained in reference example 3 was placed interior to the separating wall of the container presented in FIG. 1. The device was then tested in the same way as test example 5. All the German cockroaches (*Blattella germanica*) were still alive 7 days after the device was heated.

Test Example 7

Ten grams (10 g) of the pesticidal composition obtained in reference example 4 was placed interior to the separating wall of the container presented in FIG. 1. The example was then tested in the same way as test example 5. One German cockroach (*Blattella germanica*) was alive 7 days after the device was heated.

Test Example 8

Three samples of an apparatus wherein:
1) a piece of filter paper was placed on top of an aluminum plate,
2) an adhesive was spread on the perimeter of the said filter paper, and
3) 300 mites (*Tyrophagus putrescentiae*) were freed on top of the said filter paper were prepared. Separately, a pesticidal device was then prepared by having:
1) 10 g of the pesticidal composition obtained in example 1 placed interior to the separating wall of the container presented in FIG. 1 and
2) 100 g of calcium oxide with 1–20 mesh placed exterior to the said separating wall but within the said container.

Each said apparatus comprising of *Tyrophagus putrescentiae* was then placed at a designated location in a large chamber (28 m$^3$). The pesticidal device was then located in the central region of the large chamber. Subsequently, water was incorporated to the said calcium oxide so the device would be heated. Sixty percent (60%) of the *Tyrophagus putrescentiae* were dead one day later.

Test Example 9

Using the procedure in test example 8, the pesticidal composition obtained in reference example 4 was likewise tested for *Tyrophagus putrescentiae* control. Seventeen percent (17%) of *Tyrophagus putrescentiae* were dead one day later.

Test Example 10

Pesticidal devices were prepared in the same method as test examples 5 and 8, and had water poured to the calcium oxide. After the reaction of calcium oxide with water started, the pesticidal device was replaced to a glass funnel with a lid. The vaporizing pesticidal ingredient was then trapped to silica gel in glass column connected to the funnel by sucking air at 30 L/min for 5 m in. Subsequently, the pesticidal ingredient present in the silica gel was extracted with acetone. The vaporization rate for the pesticidal ingredient was then measured by the quantitative analysis of gas chromatography. The vaporization rate for 2-methoxycarbonyl-4-chlorotrifluoromethanesulfonanilide was 78.5%.

Test Example 11

A pesticidal device was prepared by placing:
1) 10 g of the pesticidal composition obtained in example 2 was placed interior to the separating wall of the container presented in FIG. 1 and
2) 100 g of calcium oxide with 1–20 mesh was placed exterior to the said separating wall but within the said container. The acquired pesticidal device was then tested for the vaporization rate by utilizing the procedure recited in test example 10. The vaporization rate for tetramethrin was 88.1%.

The pesticidal composition of the present invention sets forth an efficacious control of cockroaches and mites by employing a surprisingly high vaporization rate of the pesticidal ingredient. Japanese Laid-open patent No. sho-53-109945A discloses tetramethrin (Sumitomo Chemical Company Ltd. product name "Neopynamin" said publication, page 6, table 2) as having a lower vaporization rate of 63.0% (table 2, sample #23). However, when employed in the present invention, tetramethrin was able to clearly result an extraordinary high vaporization rate of 88.1%, set forth in test example 11.

Test example 5 also submits the pest repelling effectiveness of the present invention by controlling all the cockroaches. However, when the same ingredient was utilized in a separate composition such as test example 6, the pesticidal composition submits no control over the cockroaches. The high vaporization rate achieved by the present invention distributes a large dosage of the pesticidal ingredient and consequently controls pests more effectively.

What is claimed is:
1. A pesticidal composition consisting essentially of 1–25% by weight of a pesticidal ingredient, 10–97% by weight of an organic foaming agent, 0.1–10% by weight of a temperature controlling agent, and 0.1–5% by weight of a binder, wherein the pesticidal ingredient is a solid at room temperature and has a grain size of 30 µm or less in volume median diameter, and wherein the pesticidal ingredient is 2-methoxycarbonyl-4-chlorotrifluoromethanesulfonanilide, and the organic foaming agent is azodicarbonamide.

* * * * *